United States Patent
Berez et al.

(10) Patent No.: US 9,198,666 B2
(45) Date of Patent: *Dec. 1, 2015

(54) SYSTEM AND METHOD FOR DELIVERING AND DEPLOYING AN OCCLUDING DEVICE WITHIN A VESSEL

(75) Inventors: Aaron Lee Berez, Menlo Park, CA (US); Quang Quoc Tran, Redwood City, CA (US)

(73) Assignee: Covidien LP, Mansfield, MA (US)

(*) Notice: Subject to any disclaimer, the term of this patent is extended or adjusted under 35 U.S.C. 154(b) by 679 days.

This patent is subject to a terminal disclaimer.

(21) Appl. No.: 13/550,095

(22) Filed: Jul. 16, 2012

(65) Prior Publication Data

US 2012/0283815 A1    Nov. 8, 2012

Related U.S. Application Data

(60) Continuation of application No. 12/420,383, filed on Apr. 8, 2009, now Pat. No. 8,236,042, which is a division of application No. 11/136,398, filed on May 25, 2005, now Pat. No. 8,147,534.

(51) Int. Cl.
*A61F 2/06* (2013.01)
*A61B 17/12* (2006.01)
(Continued)

(52) U.S. Cl.
CPC ..... *A61B 17/12022* (2013.01); *A61B 17/12118* (2013.01); *A61F 2/966* (2013.01);
(Continued)

(58) Field of Classification Search
CPC ... A61B 17/12118; A61F 2/962; A61F 2/966; A61F 2/9665; A61F 2002/823; A61F 2/95; A61F 2002/9505–2002/9511; A61F 2002/9534; A61F 2002/9522

USPC ......... 606/191, 192, 194, 195, 198; 623/1.11, 623/1.12
See application file for complete search history.

(56) References Cited

U.S. PATENT DOCUMENTS 4,321,711 A    3/1982    Mano
4,503,569 A    3/1985    Dotter
(Continued)

FOREIGN PATENT DOCUMENTS

EP    418677    3/1991
EP    442657    8/1991
(Continued)

OTHER PUBLICATIONS

Hill, et al., "Initial Results of the Amplatzer Vascular Plug in the Treatment of Congenital Heart Disease, Business Briefing" US Cardiology, 2004.
(Continued)

*Primary Examiner* — Todd Manahan
*Assistant Examiner* — Charles Wei
(74) *Attorney, Agent, or Firm* — Mark J. Kertz, Esq.

(57) ABSTRACT

A system and method for deploying an occluding device that can be used to remodel an aneurysm within the vessel by, for example, neck reconstruction or balloon remodeling. The system comprises an introducer sheath and an assembly for carrying the occluding device. The assembly includes an elongated flexible member having an occluding device retaining member for receiving a first end of the occluding device, a proximally positioned retaining member for engaging a second end of the occluding device and a support surrounding a portion of the elongated flexible member over which the occluding device can be positioned.

18 Claims, 9 Drawing Sheets

(51) Int. Cl.
*A61F 2/966* (2013.01)
*A61F 2/82* (2013.01)

(52) U.S. Cl.
CPC ............... *A61B2017/1205* (2013.01); *A61B 2017/12054* (2013.01); *A61F 2002/823* (2013.01); *A61F 2002/9665* (2013.01)

(56) References Cited

U.S. PATENT DOCUMENTS

| | | |
|---|---|---|
| 4,512,338 A | 4/1985 | Balko et al. |
| 4,538,622 A | 9/1985 | Samson et al. |
| 4,580,568 A | 4/1986 | Gianturco |
| 4,655,771 A | 4/1987 | Wallsten |
| 4,733,665 A | 3/1988 | Palmaz |
| 4,768,507 A | 9/1988 | Fischell et al. |
| 4,776,337 A | 10/1988 | Palmaz |
| 4,954,126 A | 9/1990 | Wallsten |
| 4,998,539 A | 3/1991 | Delsanti |
| 5,011,488 A | 4/1991 | Ginsburg |
| 5,026,377 A | 6/1991 | Burton et al. |
| 5,035,706 A | 7/1991 | Giantureo et al. |
| 5,061,275 A | 10/1991 | Wallsten et al. |
| 5,064,435 A | 11/1991 | Porter |
| 5,108,416 A | 4/1992 | Ryan et al. |
| 5,147,370 A * | 9/1992 | McNamara et al. ......... 623/1.11 |
| 5,160,341 A | 11/1992 | Brenneman et al. |
| 5,180,368 A | 1/1993 | Garrison |
| 5,192,297 A | 3/1993 | Hull |
| 5,201,757 A | 4/1993 | Heyn et al. |
| 5,209,731 A | 5/1993 | Sterman et al. |
| 5,222,971 A | 6/1993 | Willard et al. |
| 5,242,399 A | 9/1993 | Lau et al. |
| 5,246,420 A | 9/1993 | Kraus et al. |
| 5,246,445 A | 9/1993 | Yachia et al. |
| 5,334,210 A | 8/1994 | Gianturco |
| 5,344,426 A | 9/1994 | Lau et al. |
| 5,360,443 A | 11/1994 | Barone et al. |
| 5,378,239 A | 1/1995 | Termin et al. |
| 5,382,259 A | 1/1995 | Phelps et al. |
| 5,401,257 A | 3/1995 | Chevalier, Jr. et al. |
| 5,405,380 A | 4/1995 | Gianotti et al. |
| 5,415,637 A | 5/1995 | Khosravi |
| 5,421,826 A | 6/1995 | Crocker et al. |
| 5,423,849 A | 6/1995 | Engelson et al. |
| 5,445,646 A | 8/1995 | Euteneuer et al. |
| 5,449,372 A | 9/1995 | Schmaltz et al. |
| 5,458,615 A | 10/1995 | Klemm et al. |
| 5,476,505 A | 12/1995 | Limon |
| 5,480,423 A | 1/1996 | Ravenscroft et al. |
| 5,484,444 A | 1/1996 | Braunschweiler et al. |
| 5,489,295 A | 2/1996 | Piplani et al. |
| 5,503,636 A | 4/1996 | Schmitt et al. |
| 5,507,768 A | 4/1996 | Lau et al. |
| 5,522,822 A | 6/1996 | Phelps et al. |
| 5,534,007 A | 7/1996 | St. Germain et al. |
| 5,545,209 A | 8/1996 | Roberts et al. |
| 5,549,635 A | 8/1996 | Solar |
| 5,562,641 A | 10/1996 | Flomenblit et al. |
| 5,562,728 A | 10/1996 | Lazarus et al. |
| 5,591,225 A | 1/1997 | Okuda |
| 5,599,291 A | 2/1997 | Balbierz et al. |
| 5,607,466 A | 3/1997 | Imbert et al. |
| 5,609,625 A | 3/1997 | Piplani et al. |
| 5,626,602 A | 5/1997 | Gianotti et al. |
| 5,628,783 A | 5/1997 | Quiachon et al. |
| 5,632,772 A | 5/1997 | Alcime et al. |
| 5,636,641 A | 6/1997 | Fariabi |
| 5,643,278 A | 7/1997 | Wijay |
| 5,662,703 A | 9/1997 | Yurek et al. |
| 5,667,522 A | 9/1997 | Flomenblit et al. |
| 5,674,276 A | 10/1997 | Andersen et al. |
| 5,683,451 A | 11/1997 | Lenker et al. |
| 5,690,120 A | 11/1997 | Jacobsen et al. |
| 5,690,644 A | 11/1997 | Yurek et al. |
| 5,695,499 A | 12/1997 | Helgerson et al. |
| 5,700,269 A | 12/1997 | Pinchuk et al. |
| 5,702,418 A | 12/1997 | Ravenscroft |
| 5,709,702 A | 1/1998 | Cogita |
| 5,709,703 A | 1/1998 | Lukic et al. |
| 5,725,552 A | 3/1998 | Kotula et al. |
| 5,725,570 A | 3/1998 | Heath |
| 5,725,571 A | 3/1998 | Imbert et al. |
| 5,733,294 A | 3/1998 | Forber et al. |
| 5,733,327 A | 3/1998 | Igaki et al. |
| 5,735,859 A | 4/1998 | Fischell et al. |
| 5,741,325 A | 4/1998 | Chaikof et al. |
| 5,741,333 A | 4/1998 | Frid |
| 5,749,883 A | 5/1998 | Halpern |
| 5,749,891 A | 5/1998 | Ken et al. |
| 5,749,919 A | 5/1998 | Blanc |
| 5,749,920 A | 5/1998 | Quiachon et al. |
| 5,769,884 A | 6/1998 | Solovay |
| 5,769,885 A | 6/1998 | Quiachon et al. |
| 5,776,099 A | 7/1998 | Tremulis |
| 5,776,140 A | 7/1998 | Cottone |
| 5,776,141 A | 7/1998 | Klein et al. |
| 5,776,142 A | 7/1998 | Gunderson |
| 5,782,909 A | 7/1998 | Quiachon et al. |
| 5,797,952 A | 8/1998 | Klein |
| 5,800,518 A | 9/1998 | Piplani et al. |
| 5,807,398 A | 9/1998 | Shaknovich |
| 5,810,837 A | 9/1998 | Hofmann et al. |
| 5,814,062 A | 9/1998 | Sepetka et al. |
| 5,817,102 A | 10/1998 | Johnson et al. |
| 5,824,039 A | 10/1998 | Piplani et al. |
| 5,824,041 A | 10/1998 | Lenker et al. |
| 5,824,044 A | 10/1998 | Quiachon et al. |
| 5,824,058 A | 10/1998 | Ravenscroft et al. |
| 5,833,632 A | 11/1998 | Jacobsen et al. |
| 5,836,868 A | 11/1998 | Ressemann et al. |
| 5,846,261 A | 12/1998 | Kotula et al. |
| 5,868,754 A | 2/1999 | Levine et al. |
| 5,873,907 A | 2/1999 | Frantzen |
| 5,888,201 A | 3/1999 | Stinson et al. |
| 5,902,266 A | 5/1999 | Leone et al. |
| 5,906,640 A | 5/1999 | Penn et al. |
| 5,911,717 A | 6/1999 | Jacobsen et al. |
| 5,916,194 A | 6/1999 | Jacobsen et al. |
| 5,916,235 A | 6/1999 | Guglielmi |
| 5,919,204 A | 7/1999 | Lukic et al. |
| 5,925,060 A | 7/1999 | Forber |
| 5,928,260 A | 7/1999 | Chin et al. |
| 5,935,148 A | 8/1999 | Villar et al. |
| 5,944,726 A | 8/1999 | Blaeser et al. |
| 5,944,738 A | 8/1999 | Amplatz et al. |
| 5,951,599 A | 9/1999 | McCrory |
| 5,957,973 A | 9/1999 | Quiachon et al. |
| 5,957,974 A | 9/1999 | Thompson et al. |
| 5,964,797 A | 10/1999 | Ho |
| 5,972,015 A | 10/1999 | Scribner et al. |
| 5,980,530 A | 11/1999 | Willard et al. |
| 5,980,533 A | 11/1999 | Holman |
| 5,980,554 A | 11/1999 | Lenker et al. |
| 5,984,929 A | 11/1999 | Bashiri et al. |
| 6,014,919 A | 1/2000 | Jacobsen et al. |
| 6,015,432 A | 1/2000 | Rakos et al. |
| 6,017,319 A | 1/2000 | Jacobsen et al. |
| 6,019,778 A | 2/2000 | Wilson et al. |
| 6,019,786 A | 2/2000 | Thompson |
| 6,022,369 A | 2/2000 | Jacobsen et al. |
| 6,024,754 A | 2/2000 | Engelson |
| 6,024,763 A | 2/2000 | Lenker et al. |
| 6,027,516 A | 2/2000 | Kolobow et al. |
| 6,033,423 A | 3/2000 | Ken et al. |
| 6,036,720 A | 3/2000 | Abrams et al. |
| 6,039,758 A | 3/2000 | Quiachon et al. |
| 6,042,589 A | 3/2000 | Marianne |
| 6,051,021 A | 4/2000 | Frid |
| 6,056,993 A | 5/2000 | Leidner et al. |
| 6,063,070 A | 5/2000 | Eder |
| 6,063,104 A | 5/2000 | Villar et al. |
| 6,063,111 A | 5/2000 | Hieshima et al. |
| 6,068,634 A | 5/2000 | Lorentzen Cornelius et al. |

(56) References Cited

U.S. PATENT DOCUMENTS

| | | |
|---|---|---|
| 6,074,407 A | 6/2000 | Levine et al. |
| 6,077,295 A | 6/2000 | Limon et al. |
| 6,086,577 A | 7/2000 | Ken et al. |
| 6,093,199 A | 7/2000 | Brown et al. |
| 6,096,052 A | 8/2000 | Callister et al. |
| 6,102,942 A | 8/2000 | Ahari |
| 6,113,607 A | 9/2000 | Lau et al. |
| 6,123,712 A | 9/2000 | Di Caprio et al. |
| 6,123,715 A | 9/2000 | Amplatz |
| 6,126,685 A | 10/2000 | Lenker et al. |
| 6,132,459 A | 10/2000 | Piplani et al. |
| 6,139,543 A | 10/2000 | Esch et al. |
| 6,139,564 A | 10/2000 | Teoh |
| 6,146,415 A | 11/2000 | Fitz |
| 6,149,680 A | 11/2000 | Shelso et al. |
| 6,152,144 A | 11/2000 | Lesh et al. |
| 6,165,178 A | 12/2000 | Bashiri et al. |
| 6,168,592 B1 | 1/2001 | Kupiecki et al. |
| 6,168,615 B1 | 1/2001 | Ken et al. |
| 6,168,618 B1 | 1/2001 | Frantzen |
| 6,168,622 B1 | 1/2001 | Mazzocchi |
| 6,183,410 B1 | 2/2001 | Jacobsen et al. |
| 6,190,402 B1 | 2/2001 | Horton et al. |
| 6,193,708 B1 | 2/2001 | Ken et al. |
| 6,197,046 B1 | 3/2001 | Piplani et al. |
| 6,206,868 B1 | 3/2001 | Parodi |
| 6,210,400 B1 | 4/2001 | Hebert et al. |
| 6,210,434 B1 | 4/2001 | Quiachon et al. |
| 6,210,435 B1 | 4/2001 | Piplani et al. |
| 6,214,038 B1 | 4/2001 | Piplani et al. |
| 6,214,042 B1 | 4/2001 | Jacobsen et al. |
| 6,221,086 B1 | 4/2001 | Forber |
| 6,221,102 B1 | 4/2001 | Baker et al. |
| 6,224,609 B1 | 5/2001 | Ressemann et al. |
| 6,224,829 B1 | 5/2001 | Piplani et al. |
| 6,231,597 B1 | 5/2001 | Deem et al. |
| 6,235,050 B1 | 5/2001 | Quiachon et al. |
| 6,241,758 B1 | 6/2001 | Cox |
| 6,241,759 B1 | 6/2001 | Piplani et al. |
| 6,245,103 B1 | 6/2001 | Stinson |
| 6,251,132 B1 | 6/2001 | Ravenscroft et al. |
| 6,260,458 B1 | 7/2001 | Jacobsen et al. |
| 6,261,305 B1 | 7/2001 | Marotta et al. |
| 6,270,523 B1 | 8/2001 | Herweck et al. |
| 6,280,465 B1 | 8/2001 | Cryer |
| 6,287,331 B1 | 9/2001 | Heath |
| 6,290,721 B1 | 9/2001 | Heath |
| 6,302,810 B2 | 10/2001 | Yokota |
| 6,302,893 B1 | 10/2001 | Limon et al. |
| 6,322,576 B1 | 11/2001 | Wallace et al. |
| 6,322,586 B1 | 11/2001 | Monroe et al. |
| 6,322,587 B1 | 11/2001 | Quiachon et al. |
| 6,331,184 B1 | 12/2001 | Abrams |
| 6,342,068 B1 | 1/2002 | Thompson |
| 6,344,041 B1 | 2/2002 | Kupiecki et al. |
| 6,344,048 B1 | 2/2002 | Chin et al. |
| 6,346,117 B1 | 2/2002 | Greenhalgh |
| 6,348,063 B1 | 2/2002 | Yassour et al. |
| 6,350,199 B1 | 2/2002 | Williams et al. |
| 6,350,270 B1 | 2/2002 | Roue |
| 6,350,278 B1 | 2/2002 | Lenker et al. |
| 6,355,061 B1 | 3/2002 | Quiachon et al. |
| 6,368,339 B1 | 4/2002 | Amplatz |
| 6,368,344 B1 | 4/2002 | Fitz |
| 6,368,557 B1 | 4/2002 | Piplani et al. |
| 6,371,928 B1 | 4/2002 | Mcfann et al. |
| 6,375,668 B1 | 4/2002 | Gifford et al. |
| 6,375,670 B1 | 4/2002 | Greenhalgh |
| 6,375,676 B1 | 4/2002 | Cox |
| 6,379,618 B1 | 4/2002 | Piplani et al. |
| 6,380,457 B1 | 4/2002 | Yurek et al. |
| 6,383,174 B1 | 5/2002 | Eder |
| 6,387,118 B1 | 5/2002 | Hanson |
| 6,391,037 B1 | 5/2002 | Greenhalgh |
| 6,395,017 B1 | 5/2002 | Dwyer et al. |
| 6,395,022 B1 | 5/2002 | Piplani et al. |
| 6,398,802 B1 | 6/2002 | Yee |
| 6,409,683 B1 | 6/2002 | Fonseca et al. |
| 6,413,235 B1 | 7/2002 | Parodi |
| 6,416,536 B1 | 7/2002 | Yee |
| 6,428,489 B1 | 8/2002 | Jacobsen et al. |
| 6,428,558 B1 | 8/2002 | Jones et al. |
| 6,432,130 B1 | 8/2002 | Hanson |
| 6,440,088 B1 | 8/2002 | Jacobsen et al. |
| 6,443,971 B1 | 9/2002 | Boylan et al. |
| 6,443,979 B1 | 9/2002 | Stalker et al. |
| 6,447,531 B1 | 9/2002 | Amplatz |
| 6,451,025 B1 * | 9/2002 | Jervis .......................... 606/108 |
| 6,454,780 B1 | 9/2002 | Wallace |
| 6,454,999 B1 | 9/2002 | Farhangnia et al. |
| 6,468,266 B1 | 10/2002 | Bashiri et al. |
| 6,478,778 B1 | 11/2002 | Jacobsen et al. |
| 6,482,221 B1 | 11/2002 | Hebert et al. |
| 6,491,648 B1 | 12/2002 | Cornish et al. |
| 6,503,450 B1 | 1/2003 | Afzal et al. |
| 6,506,204 B2 | 1/2003 | Mazzocchi |
| 6,511,468 B1 | 1/2003 | Cragg et al. |
| 6,514,261 B1 | 2/2003 | Randall et al. |
| 6,520,983 B1 | 2/2003 | Colgan et al. |
| 6,524,299 B1 | 2/2003 | Tran et al. |
| 6,527,763 B2 | 3/2003 | Esch et al. |
| 6,533,811 B1 | 3/2003 | Ryan et al. |
| 6,540,778 B1 | 4/2003 | Piplani et al. |
| 6,547,779 B2 | 4/2003 | Levine et al. |
| 6,547,804 B2 | 4/2003 | Porter et al. |
| 6,551,303 B1 | 4/2003 | Van Tassel et al. |
| 6,572,646 B1 | 6/2003 | Boylan et al. |
| 6,576,006 B2 | 6/2003 | Limon et al. |
| 6,579,303 B2 | 6/2003 | Amplatz |
| 6,582,460 B1 | 6/2003 | Cryer |
| 6,585,748 B1 | 7/2003 | Jeffree |
| 6,589,236 B2 | 7/2003 | Wheelock et al. |
| 6,589,256 B2 | 7/2003 | Forber |
| 6,589,265 B1 | 7/2003 | Palmer et al. |
| 6,589,273 B1 | 7/2003 | McDermott |
| 6,592,616 B1 | 7/2003 | Stack et al. |
| 6,599,308 B2 | 7/2003 | Amplatz |
| 6,602,280 B2 | 8/2003 | Chobotov |
| 6,605,102 B1 | 8/2003 | Mazzocchi et al. |
| 6,605,110 B2 | 8/2003 | Harrison |
| 6,605,111 B2 | 8/2003 | Bose et al. |
| 6,607,539 B1 | 8/2003 | Hayashi et al. |
| 6,607,551 B1 | 8/2003 | Sullivan et al. |
| 6,613,074 B1 | 9/2003 | Mitelberg et al. |
| 6,613,075 B1 | 9/2003 | Healy et al. |
| 6,623,518 B2 | 9/2003 | Thompson et al. |
| 6,626,939 B1 | 9/2003 | Burnside et al. |
| 6,635,068 B1 | 10/2003 | Dubrul et al. |
| 6,638,243 B2 | 10/2003 | Kupiecki |
| 6,645,240 B2 | 11/2003 | Yee |
| 6,646,218 B1 | 11/2003 | Campbell et al. |
| 6,652,508 B2 | 11/2003 | Griffin et al. |
| 6,652,556 B1 | 11/2003 | VanTassel et al. |
| 6,656,212 B2 | 12/2003 | Ravenscroft et al. |
| 6,656,218 B1 | 12/2003 | Denardo et al. |
| 6,660,024 B1 | 12/2003 | Flaherty et al. |
| 6,663,666 B1 | 12/2003 | Quiachon et al. |
| 6,666,882 B1 | 12/2003 | Bose et al. |
| 6,669,719 B2 | 12/2003 | Wallace et al. |
| 6,669,721 B1 | 12/2003 | Bose et al. |
| 6,673,089 B1 | 1/2004 | Yassour et al. |
| 6,673,100 B2 | 1/2004 | Diaz et al. |
| 6,679,893 B1 | 1/2004 | Tran |
| 6,682,546 B2 | 1/2004 | Amplatz |
| 6,682,557 B1 | 1/2004 | Quiachon et al. |
| 6,685,735 B1 | 2/2004 | Ahari |
| 6,689,162 B1 | 2/2004 | Thompson |
| 6,689,486 B2 | 2/2004 | Ho et al. |
| 6,699,274 B2 | 3/2004 | Stinson |
| 6,709,454 B1 | 3/2004 | Cox et al. |
| 6,712,834 B2 | 3/2004 | Yassour et al. |
| 6,716,238 B2 | 4/2004 | Elliott |
| 6,726,700 B1 | 4/2004 | Levine |
| 6,730,108 B2 | 5/2004 | Van Tassel et al. |

(56) References Cited

U.S. PATENT DOCUMENTS

| | | |
|---|---|---|
| 6,733,519 B2 | 5/2004 | Lashinski et al. |
| 6,740,105 B2 | 5/2004 | Yodfat et al. |
| 6,740,112 B2 | 5/2004 | Yodfat et al. |
| 6,743,219 B1 | 6/2004 | Dwyer et al. |
| 6,746,468 B1 | 6/2004 | Sepetka et al. |
| 6,746,890 B2 | 6/2004 | Gupta et al. |
| 6,755,855 B2 | 6/2004 | Yurek et al. |
| 6,758,885 B2 | 7/2004 | Leffel et al. |
| 6,767,361 B2 | 7/2004 | Quiachon et al. |
| 6,773,446 B1 | 8/2004 | Dwyer et al. |
| 6,780,196 B2 | 8/2004 | Chin et al. |
| 6,793,667 B2 | 9/2004 | Hebert et al. |
| 6,802,851 B2 | 10/2004 | Jones et al. |
| 6,811,560 B2 | 11/2004 | Jones et al. |
| 6,814,748 B1 | 11/2004 | Baker et al. |
| 6,818,006 B2 | 11/2004 | Douk et al. |
| 6,833,003 B2 | 12/2004 | Jones et al. |
| 6,849,084 B2 | 2/2005 | Rabkin et al. |
| 6,855,153 B2 | 2/2005 | Saadat |
| 6,858,034 B1 | 2/2005 | Hijlkema et al. |
| 6,860,893 B2 | 3/2005 | Wallace et al. |
| 6,860,898 B2 | 3/2005 | Stack et al. |
| 6,860,901 B1 | 3/2005 | Baker et al. |
| 6,866,677 B2 | 3/2005 | Douk et al. |
| 6,866,680 B2 | 3/2005 | Yassour et al. |
| 6,887,267 B2 | 5/2005 | Dworschak et al. |
| 6,890,337 B2 | 5/2005 | Feeser et al. |
| 6,936,055 B1 | 8/2005 | Ken et al. |
| 6,955,685 B2 | 10/2005 | Escamilla et al. |
| 6,960,227 B2 | 11/2005 | Jones et al. |
| 6,964,670 B1 | 11/2005 | Shah et al. |
| 6,976,991 B2 | 12/2005 | Hebert et al. |
| 6,989,024 B2 | 1/2006 | Hebert et al. |
| 6,994,092 B2 | 2/2006 | van der Burg et al. |
| 6,994,717 B2 | 2/2006 | Konya et al. |
| 6,994,721 B2 | 2/2006 | Israel |
| 7,001,422 B2 | 2/2006 | Escamilla et al. |
| 7,004,964 B2 | 2/2006 | Thompson et al. |
| 7,011,671 B2 | 3/2006 | Welch |
| 7,011,675 B2 | 3/2006 | Hemerick et al. |
| 7,029,487 B2 | 4/2006 | Greene, Jr. et al. |
| 7,037,330 B1 | 5/2006 | Rivelli, Jr. et al. |
| 7,066,951 B2 | 6/2006 | Chobotov |
| 7,069,835 B2 | 7/2006 | Nishri et al. |
| 7,074,236 B2 | 7/2006 | Rabkin et al. |
| 7,083,632 B2 | 8/2006 | Avellanet et al. |
| 7,093,527 B2 | 8/2006 | Rapaport et al. |
| 7,101,392 B2 | 9/2006 | Heath |
| 7,107,105 B2 | 9/2006 | Bjorklund et al. |
| 7,118,539 B2 | 10/2006 | Vrba et al. |
| 7,118,594 B2 | 10/2006 | Quiachon et al. |
| 7,122,050 B2 | 10/2006 | Randall et al. |
| 7,125,419 B2 | 10/2006 | Sequin et al. |
| 7,128,073 B1 | 10/2006 | van der Burg et al. |
| 7,128,736 B1 | 10/2006 | Abrams et al. |
| 7,137,990 B2 | 11/2006 | Hebert et al. |
| 7,166,125 B1 | 1/2007 | Baker et al. |
| 7,169,170 B2 | 1/2007 | Widenhouse |
| 7,169,172 B2 | 1/2007 | Levine et al. |
| 7,169,177 B2 | 1/2007 | Obara |
| 7,172,617 B2 | 2/2007 | Colgan et al. |
| 7,195,636 B2 | 3/2007 | Avellanet et al. |
| 7,195,639 B2 | 3/2007 | Quiachon et al. |
| 7,195,648 B2 | 3/2007 | Jones et al. |
| 7,201,768 B2 | 4/2007 | Diaz et al. |
| 7,201,769 B2 | 4/2007 | Jones et al. |
| 7,211,109 B2 | 5/2007 | Thompson |
| 7,213,495 B2 | 5/2007 | McCullagh et al. |
| 7,229,461 B2 | 6/2007 | Chin et al. |
| 7,232,461 B2 | 6/2007 | Ramer |
| 7,235,096 B1 | 6/2007 | Van Tassel et al. |
| 7,264,632 B2 | 9/2007 | Wright et al. |
| 7,275,471 B2 | 10/2007 | Nishri et al. |
| 7,279,005 B2 | 10/2007 | Stinson |
| 7,279,208 B1 | 10/2007 | Goffena et al. |
| 7,294,137 B2 | 11/2007 | Rivelli, Jr. et al. |
| 7,294,146 B2 | 11/2007 | Chew et al. |
| 7,300,456 B2 | 11/2007 | Andreas et al. |
| 7,300,460 B2 | 11/2007 | Levine et al. |
| 7,306,624 B2 | 12/2007 | Yodfat et al. |
| 7,309,351 B2 | 12/2007 | Escamilla et al. |
| 7,311,031 B2 | 12/2007 | McCullagh et al. |
| 7,320,702 B2 | 1/2008 | Hammersmark et al. |
| 7,331,973 B2 | 2/2008 | Gesswein et al. |
| 7,331,976 B2 | 2/2008 | McGuckin, Jr. et al. |
| 7,331,980 B2 | 2/2008 | Dubrul et al. |
| 7,331,985 B2 | 2/2008 | Thompson et al. |
| 7,338,518 B2 | 3/2008 | Chobotov |
| 7,419,503 B2 | 9/2008 | Pulnev et al. |
| 7,468,070 B2 | 12/2008 | Henry et al. |
| 7,470,282 B2 | 12/2008 | Shelso |
| 7,473,271 B2 | 1/2009 | Gunderson |
| 7,491,224 B2 | 2/2009 | Cox et al. |
| 7,578,826 B2 | 8/2009 | Gandhi et al. |
| 7,597,704 B2 | 10/2009 | Frazier et al. |
| 7,785,361 B2 * | 8/2010 | Nikolchev et al. ............ 623/1.11 |
| 7,862,602 B2 | 1/2011 | Licata et al. |
| 8,114,154 B2 | 2/2012 | Righini et al. |
| 8,147,534 B2 | 4/2012 | Berez et al. |
| 8,192,480 B2 | 6/2012 | Tieu et al. |
| 8,206,431 B2 | 6/2012 | Seppala et al. |
| 8,236,042 B2 | 8/2012 | Berez et al. |
| 8,257,421 B2 | 9/2012 | Berez et al. |
| 8,267,985 B2 | 9/2012 | Garcia et al. |
| 8,273,101 B2 | 9/2012 | Garcia et al. |
| 2001/0000797 A1 | 5/2001 | Mazzocchi |
| 2001/0012949 A1 | 8/2001 | Forber |
| 2001/0012961 A1 | 8/2001 | Deem et al. |
| 2001/0049547 A1 | 12/2001 | Moore |
| 2002/0013618 A1 | 1/2002 | Marotta et al. |
| 2002/0062091 A1 | 5/2002 | Jacobsen et al. |
| 2002/0078808 A1 | 6/2002 | Jacobsen et al. |
| 2002/0087119 A1 | 7/2002 | Parodi |
| 2002/0099405 A1 | 7/2002 | Yurek et al. |
| 2002/0120323 A1 | 8/2002 | Thompson et al. |
| 2002/0143384 A1 | 10/2002 | Ozasa |
| 2002/0165572 A1 | 11/2002 | Saadat |
| 2002/0169473 A1 | 11/2002 | Sepetka et al. |
| 2002/0188341 A1 | 12/2002 | Elliott |
| 2003/0028209 A1 | 2/2003 | Teoh et al. |
| 2003/0057156 A1 | 3/2003 | Peterson et al. |
| 2003/0069522 A1 | 4/2003 | Jacobsen et al. |
| 2003/0100945 A1 | 5/2003 | Yodfat et al. |
| 2003/0109887 A1 | 6/2003 | Galdonik et al. |
| 2003/0135258 A1 | 7/2003 | Andreas et al. |
| 2003/0149465 A1 | 8/2003 | Heidner et al. |
| 2003/0163155 A1 | 8/2003 | Haverkost et al. |
| 2003/0163156 A1 | 8/2003 | Hebert et al. |
| 2003/0171739 A1 | 9/2003 | Murphy et al. |
| 2003/0195553 A1 | 10/2003 | Wallace et al. |
| 2003/0199913 A1 | 10/2003 | Dubrul et al. |
| 2003/0208256 A1 | 11/2003 | DiMatteo et al. |
| 2003/0216693 A1 | 11/2003 | Mickley |
| 2004/0024416 A1 | 2/2004 | Yodfat et al. |
| 2004/0044391 A1 | 3/2004 | Porter |
| 2004/0044395 A1 | 3/2004 | Nelson |
| 2004/0049204 A1 | 3/2004 | Harari et al. |
| 2004/0049256 A1 | 3/2004 | Yee |
| 2004/0059407 A1 | 3/2004 | Escamilla et al. |
| 2004/0073300 A1 | 4/2004 | Chouinard et al. |
| 2004/0078071 A1 | 4/2004 | Escamilla et al. |
| 2004/0093063 A1 | 5/2004 | Gesswein et al. |
| 2004/0093063 A1 * | 5/2004 | Wright et al. ................ 623/1.12 |
| 2004/0122468 A1 | 6/2004 | Yodfat et al. |
| 2004/0127912 A1 * | 7/2004 | Rabkin et al. ................ 606/108 |
| 2004/0138733 A1 | 7/2004 | Weber et al. |
| 2004/0143286 A1 | 7/2004 | Johnson et al. |
| 2004/0186551 A1 | 9/2004 | Kao et al. |
| 2004/0186562 A1 | 9/2004 | Cox |
| 2004/0193178 A1 | 9/2004 | Nikolchev |
| 2004/0193179 A1 | 9/2004 | Nikolchev |
| 2004/0193206 A1 | 9/2004 | Gerberding et al. |
| 2004/0199243 A1 | 10/2004 | Yodfat |
| 2004/0204749 A1 | 10/2004 | Gunderson |

(56) References Cited

U.S. PATENT DOCUMENTS

| | | |
|---|---|---|
| 2004/0215332 A1 | 10/2004 | Frid |
| 2004/0220585 A1 | 11/2004 | Nikolchev |
| 2005/0010281 A1 | 1/2005 | Yodfat et al. |
| 2005/0033408 A1 | 2/2005 | Jones et al. |
| 2005/0033409 A1 | 2/2005 | Burke et al. |
| 2005/0049668 A1 | 3/2005 | Jones et al. |
| 2005/0049670 A1 | 3/2005 | Jones et al. |
| 2005/0090890 A1 | 4/2005 | Wu et al. |
| 2005/0096728 A1 | 5/2005 | Ramer |
| 2005/0096732 A1 | 5/2005 | Marotta et al. |
| 2005/0107823 A1 | 5/2005 | Leone et al. |
| 2005/0131523 A1 | 6/2005 | Bashiri et al. |
| 2005/0137680 A1 | 6/2005 | Ortiz et al. |
| 2005/0209672 A1 | 9/2005 | George et al. |
| 2005/0228434 A1 | 10/2005 | Amplatz et al. |
| 2005/0246010 A1 | 11/2005 | Alexander et al. |
| 2005/0267568 A1 | 12/2005 | Berez et al. |
| 2005/0283220 A1 | 12/2005 | Gobran et al. |
| 2005/0283222 A1 | 12/2005 | Betelia et al. |
| 2005/0288764 A1 | 12/2005 | Snow et al. |
| 2005/0288766 A1 | 12/2005 | Plain et al. |
| 2006/0036309 A1 | 2/2006 | Hebert et al. |
| 2006/0052815 A1 | 3/2006 | Fitz et al. |
| 2006/0052816 A1 | 3/2006 | Bates et al. |
| 2006/0058865 A1 | 3/2006 | Case et al. |
| 2006/0064151 A1 | 3/2006 | Guterman et al. |
| 2006/0089703 A1 | 4/2006 | Escamilla et al. |
| 2006/0095213 A1 | 5/2006 | Escamilla et al. |
| 2006/0111771 A1 | 5/2006 | Ton et al. |
| 2006/0116714 A1 | 6/2006 | Sepetka et al. |
| 2006/0116750 A1 | 6/2006 | Hebert et al. |
| 2006/0155323 A1 | 7/2006 | Porter et al. |
| 2006/0167494 A1 | 7/2006 | Suddaby |
| 2006/0184238 A1 | 8/2006 | Kaufmann et al. |
| 2006/0190076 A1 | 8/2006 | Taheri |
| 2006/0206200 A1 | 9/2006 | Garcia et al. |
| 2006/0206201 A1 | 9/2006 | Garcia et al. |
| 2006/0212127 A1 | 9/2006 | Karabey et al. |
| 2006/0235464 A1 | 10/2006 | Avellanet et al. |
| 2006/0235501 A1 | 10/2006 | Igaki |
| 2006/0247680 A1 | 11/2006 | Amplatz et al. |
| 2006/0271149 A1 | 11/2006 | Berez et al. |
| 2006/0271153 A1 | 11/2006 | Garcia et al. |
| 2007/0021816 A1 | 1/2007 | Rudin |
| 2007/0043419 A1 | 2/2007 | Nikolchev et al. |
| 2007/0055339 A1 | 3/2007 | George et al. |
| 2007/0073379 A1 | 3/2007 | Chang |
| 2007/0088387 A1 | 4/2007 | Eskridge et al. |
| 2007/0100414 A1 | 5/2007 | Licata et al. |
| 2007/0106311 A1 | 5/2007 | Wallace et al. |
| 2007/0112415 A1 | 5/2007 | Bartlett |
| 2007/0119295 A1 | 5/2007 | McCullagh et al. |
| 2007/0123969 A1 | 5/2007 | Gianotti |
| 2007/0162104 A1 | 7/2007 | Frid |
| 2007/0167980 A1 | 7/2007 | Figulla et al. |
| 2007/0191884 A1 | 8/2007 | Eskridge et al. |
| 2007/0198075 A1 | 8/2007 | Levy |
| 2007/0198076 A1 | 8/2007 | Hebert et al. |
| 2007/0203559 A1 | 8/2007 | Freudenthal et al. |
| 2007/0203563 A1 | 8/2007 | Hebert et al. |
| 2007/0203567 A1 | 8/2007 | Levy |
| 2007/0208376 A1 | 9/2007 | Meng |
| 2007/0221230 A1 | 9/2007 | Thompson et al. |
| 2007/0225760 A1 | 9/2007 | Moszner et al. |
| 2007/0225794 A1 | 9/2007 | Thramann et al. |
| 2007/0239261 A1 | 10/2007 | Bose et al. |
| 2007/0265656 A1 | 11/2007 | Amplatz et al. |
| 2007/0270902 A1 | 11/2007 | Slazas et al. |
| 2007/0288083 A1 | 12/2007 | Hines |
| 2007/0299500 A1 | 12/2007 | Hebert et al. |
| 2007/0299501 A1 | 12/2007 | Hebert et al. |
| 2007/0299502 A1 | 12/2007 | Hebert et al. |
| 2008/0003354 A1 | 1/2008 | Nolan |
| 2008/0021535 A1 | 1/2008 | Leopold et al. |
| 2008/0039933 A1 | 2/2008 | Yodfat et al. |
| 2008/0082154 A1 | 4/2008 | Tseng et al. |
| 2008/0097495 A1 | 4/2008 | Feller, III et al. |
| 2008/0119886 A1 | 5/2008 | Greenhalgh et al. |
| 2008/0154286 A1 | 6/2008 | Abbott et al. |
| 2008/0195139 A1 | 8/2008 | Donald et al. |
| 2008/0208320 A1 | 8/2008 | Tan-Malecki et al. |
| 2008/0219533 A1 | 9/2008 | Grigorescu |
| 2008/0221600 A1 | 9/2008 | Dieck et al. |
| 2008/0221666 A1* | 9/2008 | Licata et al. ................. 623/1.22 |
| 2008/0255654 A1 | 10/2008 | Hebert et al. |
| 2008/0262590 A1 | 10/2008 | Murray |
| 2008/0269774 A1 | 10/2008 | Garcia et al. |
| 2008/0281350 A1 | 11/2008 | Sepetka et al. |
| 2008/0300667 A1 | 12/2008 | Hebert et al. |
| 2008/0319533 A1 | 12/2008 | Lehe |
| 2009/0024202 A1 | 1/2009 | Dave et al. |
| 2009/0024205 A1 | 1/2009 | Hebert et al. |
| 2009/0025820 A1 | 1/2009 | Adams |
| 2009/0030496 A1 | 1/2009 | Kaufmann et al. |
| 2009/0030497 A1 | 1/2009 | Metcalf et al. |
| 2009/0082803 A1 | 3/2009 | Adams et al. |
| 2009/0105802 A1 | 4/2009 | Henry et al. |
| 2009/0105803 A1 | 4/2009 | Shelso |
| 2009/0112251 A1 | 4/2009 | Qian et al. |
| 2009/0125093 A1 | 5/2009 | Hansen |
| 2009/0138065 A1 | 5/2009 | Zhang et al. |
| 2009/0163986 A1 | 6/2009 | Tieu et al. |
| 2009/0192536 A1 | 7/2009 | Berez et al. |
| 2009/0210047 A1 | 8/2009 | Amplatz et al. |
| 2009/0264978 A1 | 10/2009 | Dieck et al. |
| 2009/0270974 A1 | 10/2009 | Berez et al. |
| 2009/0275974 A1 | 11/2009 | Marchand et al. |
| 2009/0287241 A1 | 11/2009 | Berez et al. |
| 2009/0287288 A1 | 11/2009 | Berez et al. |
| 2009/0287292 A1 | 11/2009 | Becking et al. |
| 2009/0292348 A1 | 11/2009 | Berez et al. |
| 2009/0318947 A1 | 12/2009 | Garcia et al. |
| 2009/0319017 A1 | 12/2009 | Berez et al. |
| 2010/0030220 A1 | 2/2010 | Truckai et al. |
| 2010/0069948 A1 | 3/2010 | Veznedaroglu et al. |
| 2010/0152767 A1 | 6/2010 | Greenhalgh et al. |
| 2010/0268204 A1 | 10/2010 | Tieu et al. |
| 2010/0305606 A1 | 12/2010 | Gandhi et al. |
| 2010/0331948 A1 | 12/2010 | Turovskiy et al. |
| 2011/0313447 A1 | 12/2011 | Strauss et al. |
| 2012/0041470 A1 | 2/2012 | Shrivastava et al. |
| 2012/0041474 A1 | 2/2012 | Eckhouse et al. |
| 2012/0065720 A1 | 3/2012 | Strauss et al. |
| 2012/0221095 A1 | 8/2012 | Berez et al. |
| 2012/0277784 A1 | 11/2012 | Berez et al. |
| 2012/0283765 A1 | 11/2012 | Berez et al. |
| 2012/0283815 A1 | 11/2012 | Berez et al. |
| 2013/0144380 A1 | 6/2013 | Quadri et al. |
| 2013/0172976 A1 | 7/2013 | Garcia et al. |

FOREIGN PATENT DOCUMENTS

| | | |
|---|---|---|
| EP | 696447 A2 | 2/1996 |
| EP | 1369098 | 12/2003 |
| EP | 1400219 | 3/2004 |
| EP | 1621148 | 2/2006 |
| EP | 2 143 404 | 1/2010 |
| EP | 2 143 460 | 1/2010 |
| JP | 10-328216 A | 12/1998 |
| JP | 11-299901 A | 11/1999 |
| JP | 2001-509412 A | 7/2001 |
| JP | 2005-074230 A | 3/2005 |
| WO | WO-95/09586 | 4/1995 |
| WO | WO-97/26939 | 7/1997 |
| WO | WO-98/09583 A2 | 3/1998 |
| WO | WO-99/02092 | 1/1999 |
| WO | WO-99/03404 | 1/1999 |
| WO | WO-99/05977 | 2/1999 |
| WO | WO-99/49812 | 10/1999 |
| WO | WO-99/62432 | 12/1999 |
| WO | WO-00/13593 | 3/2000 |
| WO | WO-01/05331 | 1/2001 |
| WO | WO-01/93782 | 12/2001 |
| WO | WO-02/00139 | 1/2002 |

(56) References Cited

FOREIGN PATENT DOCUMENTS

| WO | WO-02/28320 A2 | 4/2002 |
| WO | WO-02/056798 A2 | 7/2002 |
| WO | WO-02/060345 A2 | 8/2002 |
| WO | WO-02/071977 A2 | 9/2002 |
| WO | WO-03/007840 | 1/2003 |
| WO | WO-03/022124 | 3/2003 |
| WO | WO-03/049600 | 6/2003 |
| WO | WO-2004/010878 A1 | 2/2004 |
| WO | WO-2004/030575 | 4/2004 |
| WO | WO-2004/066809 A2 | 8/2004 |
| WO | WO-2004/087006 A3 | 11/2004 |
| WO | WO-2005/018728 A2 | 3/2005 |
| WO | WO-2005/030093 | 4/2005 |
| WO | WO-2005/115118 | 12/2005 |
| WO | WO-2005/117718 | 12/2005 |
| WO | WO-2006/026744 | 3/2006 |
| WO | WO-2006/052322 A2 | 5/2006 |
| WO | WO-2006/091891 A2 | 8/2006 |
| WO | WO-2006/127005 | 11/2006 |
| WO | WO-2007/121405 | 10/2007 |
| WO | WO-2008/022327 A2 | 2/2008 |
| WO | WO-2008/151204 | 12/2008 |
| WO | WO-2008/157507 A2 | 12/2008 |
| WO | WO-2009/134337 | 11/2009 |
| WO | WO-2010/030991 | 3/2010 |
| WO | WO-2011/130081 A1 | 10/2011 |

OTHER PUBLICATIONS

Ronen, "Amplatzer Vascular Plug Case Study, Closure of Arteriovenous Fistula Between Deep Femoral Artery and Superficial Femoral Vein," AGA Medical Corporation, May 2007.

Benndorf et al., "Treatment of ruptured dissecting vertebral artery anneurysm with double stent placement: case report," Am J Neuroradiol., Dec. 2001, vol. 22, No. 10, pp. 1844-1848.

Brilstra et al., Treatment of Intercranial Aneurysms by Emboloization with Coils: A Systematic Review, Stroke, 1999, vol. 30, pp. 470-476.

Ferguson, "Physical Factors in the Initiation, Growth and Rupture of Human Intracranial Saccular Aneurysms," J Neurosurg., 1972, vol. 37, pp. 666-677.

Geremia et al., "Embolization of experimentally created aneurysms with intravascular stent devices," Am J. Neuroradiol., Aug. 1994, vol. 15, No. 7, pp. 1223-1231.

Geremia et al., "Occlusion of experimentally created fusiform aneurysms with porous metallic stents," Am J Neuroradiol., Apr. 2000, vol. 4, pp. 739-745.

Lanzino et al., "Efficacy and current limitations of intravascular stents for intracranial internal cartoid, vertebral, and basilar artery aneurysms," J Neurosurg., 1999, vol. 91, pp. 538-546.

Lieber et al, "The Physics of Endoluminal Stenting in the Treatment of Cerebrovascular Aneurysms," Neurological Research, 2002, vol. 24, Supplement 1, pp. S32-S42.

Lieber et al., "Alteration of Hemodynamics in Aneurysm Models by Stenting: Influence of Stent Porosity," Ann of Biomedical Eng., 1997, vol. 25, p. 460.

Moss, "Vascular Occulusion with a Balloon-Expandable Stent Occluder," Radiology, vol. 191, No. 2, May 1994, pp. 483-486.

Pereira, "History of Endovascular Aneurysms Occlusion in Management of Cerebral Aneurysms," Eds: Le Roux et al., 2004, pp. 11-26.

Qureshi, "Endovascular Treatment of Cerebrovascular Diseases and Intracranial Neoplasms," The Lancet, Mar. 2004, vol. 363, pp. 804-813.

Steiger, "Pathophysiology of Development and Rupture of Cerebral Aneurysms," Acta Neurochir Suppl., 1990, vol. 48, pp. 1-57.

Tenaglia, A. "Ultrasound Guide Wire-Directed Stent Deployment," Duke Univ. Medical Center, Department of Medicine, Am Heart J., 1993.

Yu et al., "A steady flow analysis on the stented and non-stented sdewall aneurysm models," Med Eng Phys., Apr. 1999, vol. 21, No. 3, 133-141.

* cited by examiner

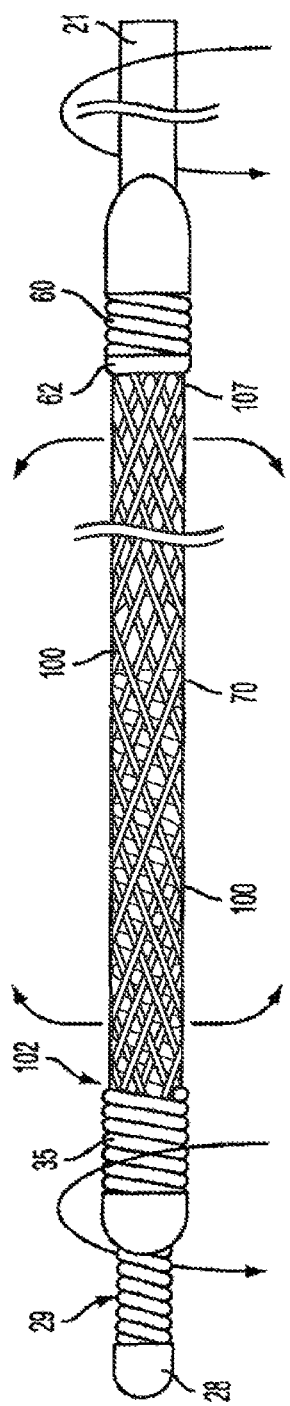

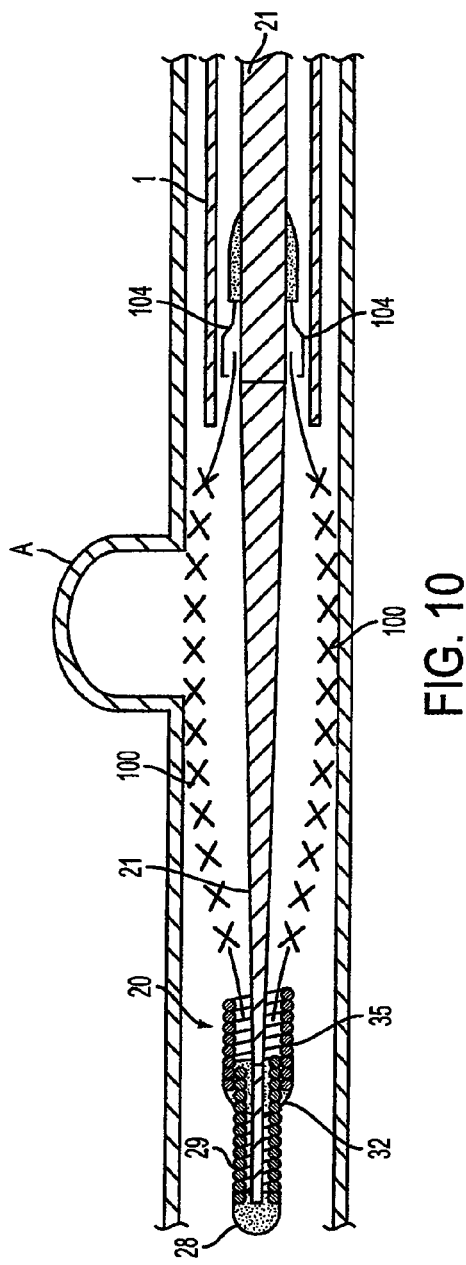
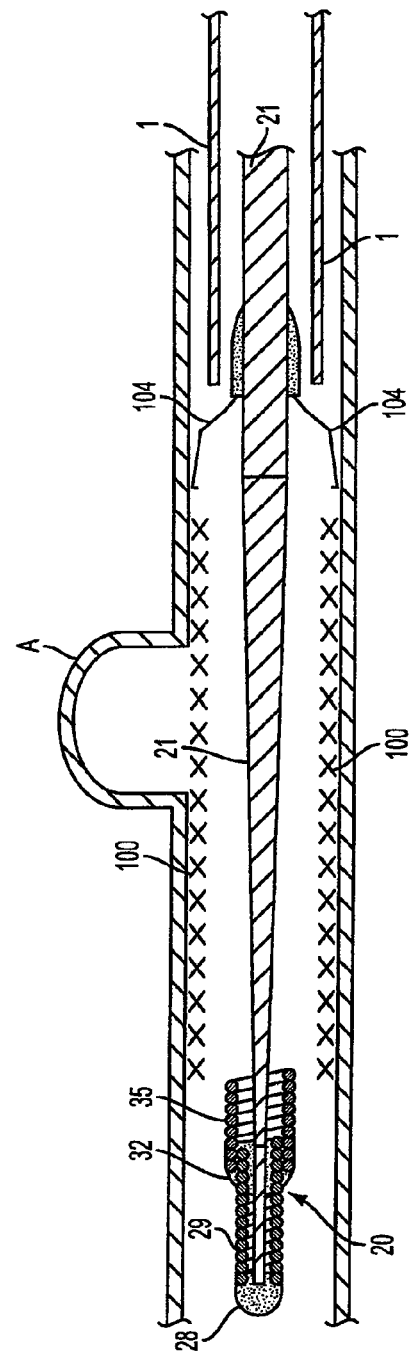
FIG. 10
FIG. 11

SYSTEM AND METHOD FOR DELIVERING AND DEPLOYING AN OCCLUDING DEVICE WITHIN A VESSEL

CROSS-REFERENCE TO RELATED APPLICATIONS

This application is a continuation of U.S. patent application Ser. No. 12/420,383, filed Apr. 8, 2009, which is a divisional of U.S. patent application Ser. No. 11/136,398, filed May 25, 2005, both of which are expressly incorporated herein by reference in their entireties.

FIELD

The invention generally relates to a system and method for delivering and deploying a medical device within a vessel, more particularly, it relates to a system and method for delivering and deploying an endoluminal therapeutic device within the vasculature of a patient to embolize and occlude aneurysms, particularly cerebral aneurysms.

BACKGROUND

Walls of the vasculature, particularly arterial walls, may develop areas of pathological dilatation called aneurysms. As is well known, aneurysms have thin, weak walls that are prone to rupturing. Aneurysms can be the result of the vessel wall being weakened by disease, injury or a congenital abnormality. Aneurysms could be found in different parts of the body with the most common being abdominal aortic aneurysms and brain or cerebral aneurysms in the neurovasculature. When the weakened wall of an aneurysm ruptures, it can result in death, especially if it is a cerebral aneurysm that ruptures.

Aneurysms are generally treated by excluding the weakened part of the vessel from the arterial circulation. For treating a cerebral aneurysm, such reinforcement is done in many ways including: (i) surgical clipping, where a metal clip is secured around the base of the aneurysm; (ii) packing the aneurysm with small, flexible wire coils (micro-coils); (iii) using embolic materials to "fill" an aneurysm; (iv) using detachable balloons or coils to occlude the parent vessel that supplies the aneurysm; and (v) intravascular stenting.

Intravascular stents are well known in the medical arts for the treatment of vascular stenoses or aneurysms. Stents are prostheses that expand radially or otherwise within a vessel or lumen to provide support against the collapse of the vessel. Methods for delivering these intravascular stents are also well known.

In conventional methods of introducing a compressed stent into a vessel and positioning it within in an area of stenosis or an aneurysm, a guiding catheter having a distal tip is percutaneously introduced into the vascular system of a patient. The guiding catheter is advanced within the vessel until its distal tip is proximate the stenosis or aneurysm. A guidewire positioned within an inner lumen of a second, inner catheter and the inner catheter are advanced through the distal end of the guiding catheter. The guidewire is then advanced out of the distal end of the guiding catheter into the vessel until the distal portion of the guidewire carrying the compressed stent is positioned at the point of the lesion within the vessel. Once the compressed stent is located at the lesion, the stent may be released and expanded so that it supports the vessel.

SUMMARY

Aspects of the present invention include a system and method of deploying an occluding device within a vessel. The occluding device can be used to remodel an aneurysm within the vessel by, for example, neck reconstruction or balloon remodeling. The occluding device can be used to form a barrier that retains occlusion material such as a well known coil or viscous fluids, such as "ONYX" by Microtherapeutics, within the aneurysm so that introduced material will not escape from within the aneurysm. Also, during deployment, the length of the occluding device can be adjusted in response to friction created between the occluding device and an inner surface of a catheter. When this occurs, the deployed length and circumferential size of the occluding device can be changed as desired by the physician performing the procedure.

An aspect of the present invention includes a system for supporting and deploying an occluding device. The system comprises an introducer sheath and an assembly for carrying the occluding device. The assembly includes an elongated flexible member having an occluding device retaining member for receiving a first end of the occluding device, a proximally positioned retaining member for engaging a second end of the occluding device and a support surrounding a portion of the elongated flexible member over which the occluding device can be positioned.

Another aspect of the present invention includes a system for supporting and deploying an occluding device. The system comprises an assembly for carrying the occluding device. The assembly comprises an elongated member including a flexible distal tip portion, a retaining member for receiving a first end of the occluding device, and a support surrounding a portion of the elongated flexible member for supporting the occluding device.

A further aspect of the present invention comprises a method of introducing and deploying an occluding device within a vessel. The method includes the steps of introducing an elongated sheath including an introducer sheath carrying a guidewire assembly into a catheter and advancing the guidewire assembly out of the sheath and into the catheter. The method also includes the steps of positioning an end of the catheter proximate an aneurysm, advancing a portion of the guidewire assembly out of the catheter and rotating a portion of the guidewire assembly while deploying the occluding device in the area of the aneurysm.

BRIEF DESCRIPTION OF THE FIGURES

FIG. 8 illustrates a step in the method of deploying the occluding device;

FIG. 10 is a schematic view of a guidewire assembly according to another embodiment of the present invention; and FIG. 11 is a schematic view of the deployed occluding device after having been deployed by the guidewire assembly of FIG. 10.

DETAILED DESCRIPTION

Figure 1:
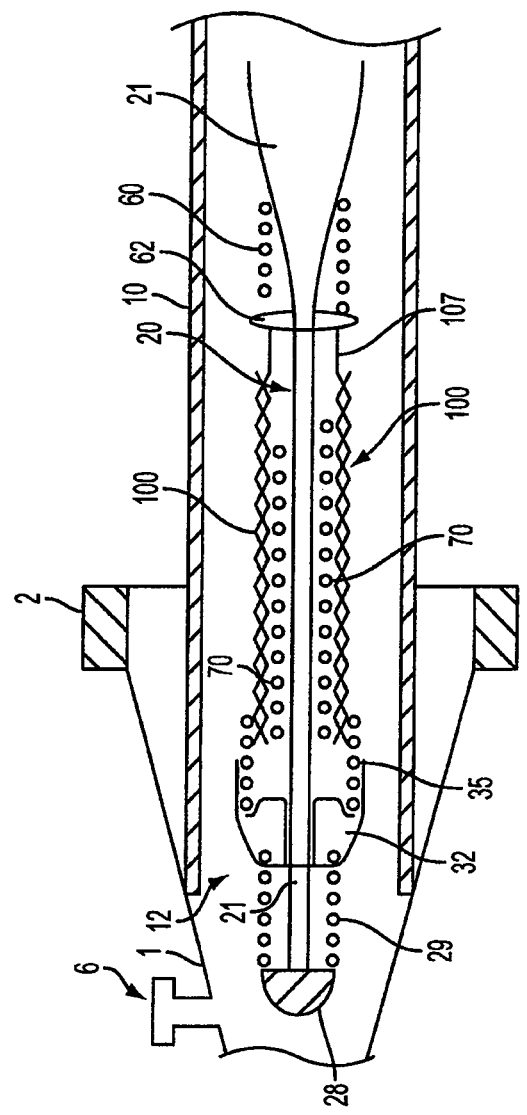
FIG. 1 is a cross section of an occluding device delivery assembly and occluding device according to an aspect of the invention.

An occluding device delivery assembly having portions with small cross section(s) and which is highly flexible is described herein. FIG. 1 illustrates an introducer sheath 10 according to an aspect of the present invention that receives, contains and delivers an occluding device 100 to a flexible micro-catheter 1 for positioning within the vasculature of an individual. The occluding device 100 can include those embodiments disclosed in copending U.S. patent application Ser. No. 11/136,395, titled "Flexible Vascular Occluding Device", filed on May 25, 2005, which is expressly hereby incorporated by reference in its entirety.

Figure 2:
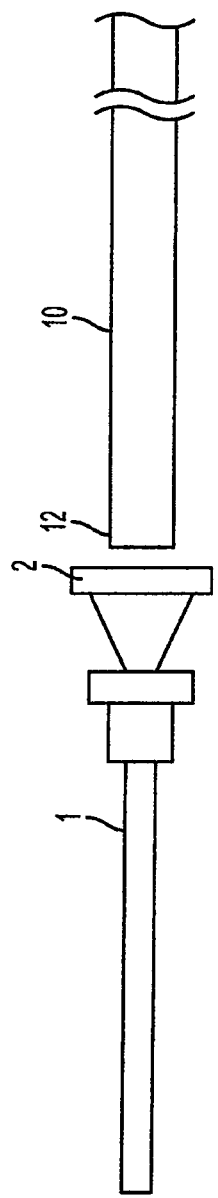
FIG. 2 illustrates a catheter and introducer sheath shown in FIG. 1.

A distal end 12 of the introducer sheath 10 is sized and configured to be received within a hub 2 of the micro-catheter 1, as shown in FIGS. 1 and 2. The hub 2 can be positioned at the proximal end of the micro-catheter 1 or at another location spaced along the length of the micro-catheter 1. The micro-catheter 1 can be any known micro-catheter that can be introduced and advanced through the vasculature of a patient. In an embodiment, the micro-catheter has an inner diameter of 0.047 inch or less. In another embodiment, the micro-catheter has an inner diameter of about 0.027 inch to about 0.021 inch. In an alternative embodiment, the micro-catheter could have an inner diameter of about 0.025 inch. However, it is contemplated that the catheter 1 can have an inner diameter that is greater than 0.047 inch or less than 0.021 inch. After the introducer sheath 10 is positioned within the catheter hub 2, the occluding device 100 can be advanced from the introducer sheath 10 into the micro-catheter 1 in preparation for deploying the occluding device 100 within the vasculature of the patient.

The micro-catheter 1 may have at least one fluid introduction port 6 located adjacent the hub 2 or at another position along its length. The port 6 is preferably in fluid communication with the distal end of the micro-catheter 1 so that a fluid, e.g., saline, may be passed through the micro-catheter 1 prior to insertion into the vasculature for flushing out air or debris trapped within the micro-catheter 1 and any instruments, such as guidewires, positioned within the micro-catheter 1. The port 6 may also be used to deliver drugs or fluids within the vasculature as desired.

Figure 3:
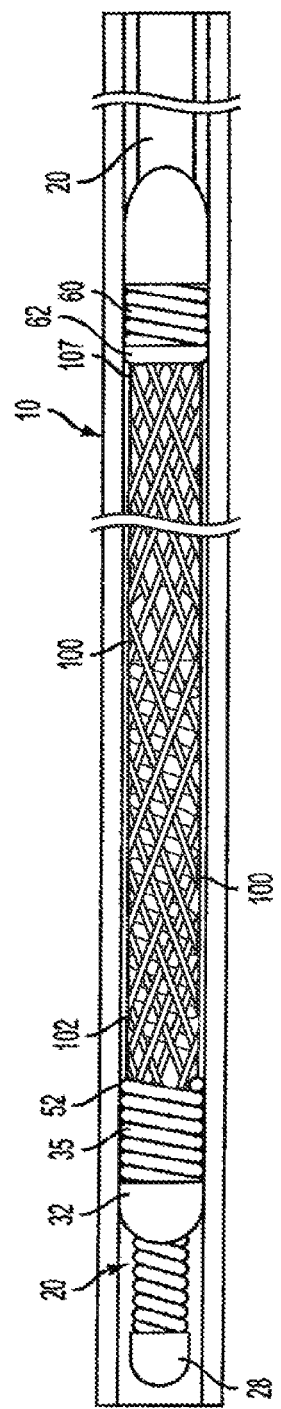
FIG. 3 is a partial cut away view of the introducer sheath of FIG. 2 carrying a guidewire assembly loaded with an occluding device.

FIG. 3 illustrates the introducer sheath 10, an elongated flexible delivery guidewire assembly 20 that is movable within the introducer sheath 10 and the occluding device 100. As shown, the guidewire assembly 20 and the occluding device 100, carried by the guidewire assembly 20, have not been introduced into the micro-catheter 1. Instead, as illustrated, they are positioned within the introducer sheath 10. The introducer sheath 10 may be made from various thermoplastics, e.g., PTFE, FEP, HDPE, PEEK, etc., which may optionally be lined on the inner surface of the sheath or an adjacent surface with a hydrophilic material such as PVP or some other plastic coating. Additionally, either surface may be coated with various combinations of different materials, depending upon the desired results.

The introducer sheath 10 may include drainage ports or purge holes (not shown) formed into the wall near the area covering the occluding device 100. There may be a single hole or multiple holes, e.g., three holes, formed into introducer sheath 10. These purge holes allow for fluids, e.g., saline, to readily escape from in between the introducer sheath 10 and the guidewire assembly 20 when purging the sheath prior to positioning the introducer sheath 10 in contact with the catheter hub 2, e.g., to remove trapped air or debris.

Figure 4:
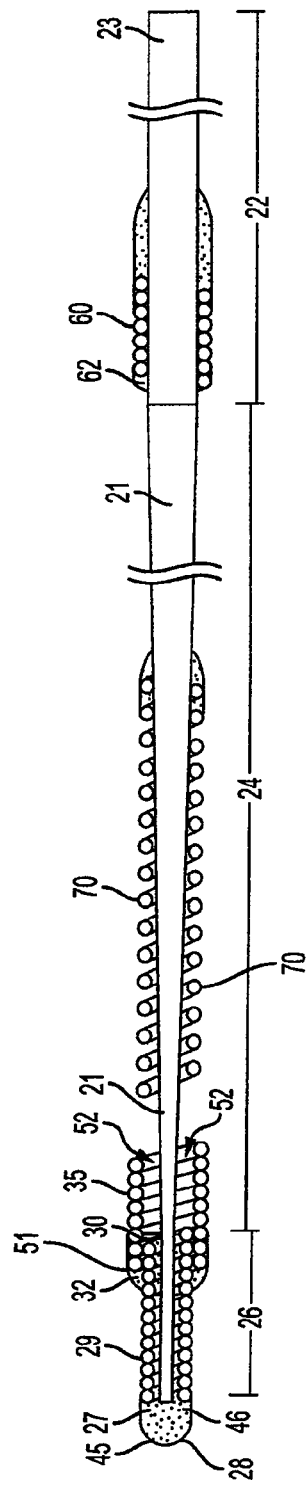
FIG. 4 is a cross section of the guidewire assembly illustrated in FIG. 3.

As shown in FIG. 4, the guidewire assembly 20 includes an elongated flexible guidewire 21. The flexibility of the guidewire 21 allows the guidewire assembly to bend and conform to the curvature of the vasculature as needed for positional movement of the occluding device 100 within the vasculature. The guidewire 21 may be made of a conventional guidewire material and have a solid cross section. Alternatively, the guidewire 21 can be formed from a hypotube. In either embodiment, the guidewire 21 has a diameter $D_5$ ranging from about 0.010 inch to about 0.020 inch. In an embodiment, the largest diameter of the guidewire is about 0.016 inch. The material used for the guidewire 21 can be any of the known guidewire materials including superelastic metals, e.g., Nitinol. Alternatively, the guidewire 21 can be formed of metals such as stainless steel. Length $L_4$ of the guidewire can be from about 125 to about 190 cm. In an embodiment, the length $L_4$ is about 175 cm.

The guidewire assembly 20 can have the same degree of flexion along its entire length. In an alternative embodiment, the guidewire assembly 20 can have longitudinal sections, each with differing degrees of flexion/stiffness. The different degrees of flexions for the guidewire assembly 20 can be created using different materials and/or thicknesses within different longitudinal sections of the guidewire 21. In another embodiment, the flexion of the guidewire 21 can be controlled by spaced cuts (not shown) formed within the delivery guidewire 21. These cuts can be longitudinally and/or circumferentially spaced from each other. The cuts can be formed with precision within the delivery guidewire 21. Different sections of the delivery guidewire 21 can include cuts formed with different spacing and different depths to provide these distinct sections with different amounts of flexion and stiffness. In any of the above embodiments, the guidewire assembly 20 and the guidewire 21 are responsive to torque applied to the guidewire assembly 20 by the operator. As discussed below, the torque applied to the guidewire assembly 20 via the guidewire 21 can be used to release the occluding device 100 from the guidewire assembly 20.

The size and shape of the cuts formed within the delivery guidewire 21 may be controlled so as to provide greater or lesser amounts of flexibility. Because the cuts can be varied in width without changing the depth or overall shape of the cut, the flexibility of the delivery guidewire 21 may be selectively altered without affecting the torsional strength of the delivery guidewire 21. Thus, the flexibility and torsional strength of the delivery guidewire 21 may be selectively and independently altered.

Advantageously, longitudinally adjacent pairs of cuts may be rotated about 90 degrees around the circumference of the delivery guidewire 21 from one another to provide flexure laterally and vertically. However, the cuts may be located at predetermined locations to provide preferential flexure in one or more desired directions. Of course, the cuts could be randomly formed to allow bending (flexion) equally, non-preferentially in all directions or planes. In one embodiment, this could be achieved by circumferentially spacing the cuts.

The flexible delivery guidewire 21 can include any number of sections having the same or differing degrees of flexion. For example, the flexible delivery guidewire 21 could include two or more sections. In the embodiment illustrated in FIG. 4, the flexible delivery guidewire 21 includes three sections, each having a different diameter. Each section can have a diameter of about 0.005 inch to about 0.025 inch. In an embodiment, the diameter of one or more sections can be about 0.010 inch to about 0.020 inch. A first section 22 includes a proximal end 23 that is located opposite the position of the occluding device 100. The first section 22 can have a constant thickness along its length. Alternatively, the first section 22 can have a thickness (diameter) that tapers along its entire length or only a portion of its length. In the tapered embodiment, the thickness (diameter) of the first section 22 decreases in the direction of a second, transition section 24. For those embodiments in which the guidewire 21 has a circular cross section, the thickness is the diameter of the section.

The second, transition section 24 extends between the first section 22 and a third, distal section 26. The second section 24 tapers in thickness from the large diameter of the first section 22 to the smaller diameter of the third section 26. As with the first section 22, the second section 24 can taper along its entire length or only a portion of its length.

The third section 26 has a smaller thickness compared to the other sections 22, 24 of the delivery guidewire 21. The third section 26 extends, away from the tapered second section 24 that carries the occluding device 100. The third section 26 can taper along its entire length from the second section 24 to the distal end 27 of the delivery guidewire 21. Alternatively, the third section 26 can have a constant diameter or taper along only a portion of its length. In such an embodiment, the tapering portion of the third section 26 can extend from the second section 24 or a point spaced from the second section 24 to a point spaced from distal end 27 of the delivery guidewire 21. Although three sections of the delivery guidewire 21 are discussed and illustrated, the delivery guidewire 21 can include more than three sections. Additionally, each of these sections can taper in their thickness (diameter) along all or only a portion of their length. In any of the disclosed embodiments, the delivery guidewire 21 can be formed of a shape memory alloy such as Nitinol.

Figure 5:
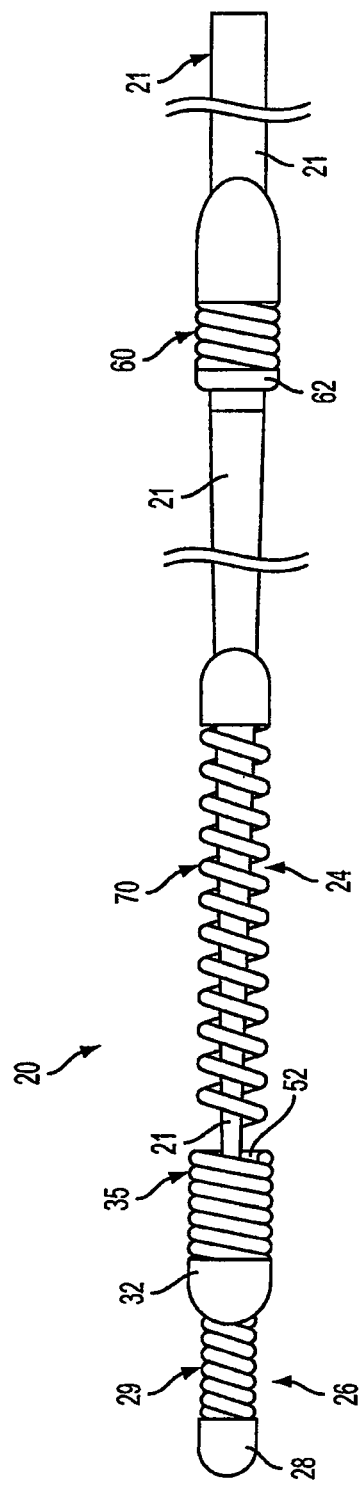
FIG. 5 is a schematic view of the guidewire assembly of FIG. 4.
Figure 6:
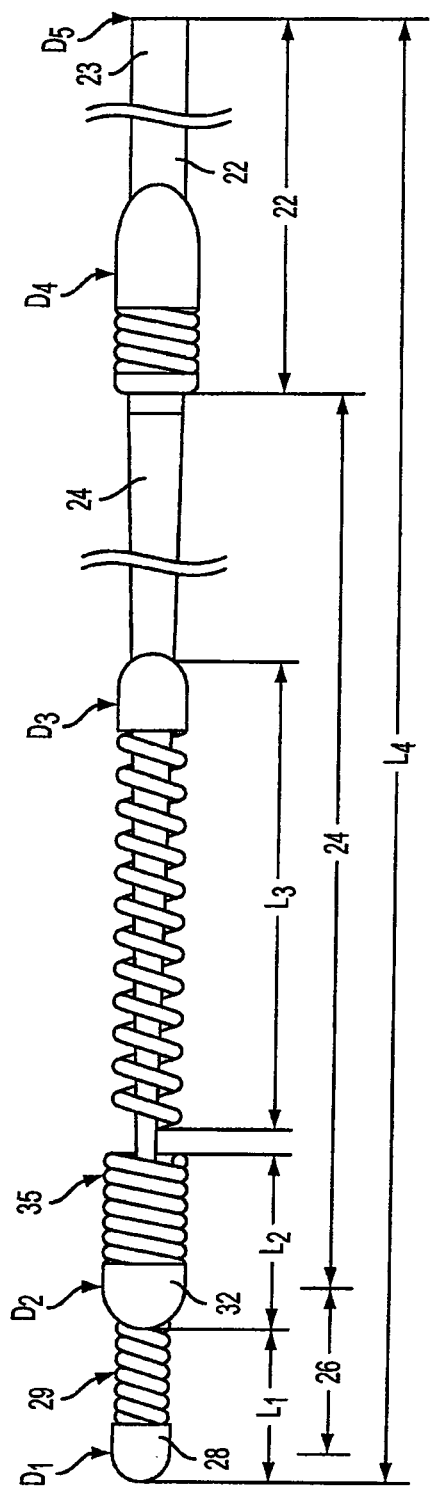
FIG. 6 is a second schematic view of the guidewire assembly of FIG. 4.

A tip 28 and flexible tip coil 29 are secured to the distal end 27 of the delivery guidewire 21 as shown in FIGS. 4 and 5. The tip 28 can include a continuous end cap or cover as shown in the figures, which securely receives a distal end of the tip coil 29. Flexion control is provided to the distal end portion of the delivery guidewire 21 by the tip coil 29. However, in an embodiment, the tip 28 can be free of the coil 29. The tip 28 has a non-percutaneous, atraumatic end face. In the illustrated embodiment, the tip 28 has a rounded face. In alternative embodiments, the tip 28 can have other non-percutaneous shapes that will not injure the vessel in which it is introduced. As illustrated in FIG. 4, the tip 28 includes a housing 45 that securely receives the distal end of the guidewire 21 within an opening 46 in the interior surface of the housing 45. The guidewire 21 can be secured within the opening by any known means.

As shown in FIG. 4, the tip coil 29 surrounds a portion of the guidewire 21. The tip coil 29 is flexible so that it will conform to and follow the path of a vessel within the patient as the tip 28 is advanced along the vessel and the guidewire 21 bends to follow the tortuous path of the vasculature. The tip coil 29 extends rearward from the tip 28 in the direction of the proximal end 23, as shown.

The tip 28 and coil 29 have an outer diameter $D_1$ of about 0.010 inch to about 0.018 inch. In an embodiment, their outer diameter $D_1$ is about 0.014 inch. The tip 28 and coil 29 also have a length $L_1$ of about 0.1 cm to about 3.0 cm. In an embodiment, they have a total length $L_1$ of about 1.5 cm.

A proximal end 30 of the tip coil 29 is received within a housing 32 at a distal end 24 of a protective coil 35, as shown in FIGS. 1 and 4. The housing 32 and protective coil 35 have an outer diameter D2 of about 0.018 inch to about 0.038 inch. In an embodiment, their outer diameter $D_2$ is about 0.024 inch. The housing 32 and protective coil 35 have a length L2 of about 0.05 cm to about 0.2 cm. In an embodiment, their total length L2 is about 0.15 cm.

The housing 32 has a non-percutaneous, atraumatic shape. For example, as shown in FIG. 5, the housing 32 has a substantially blunt profile. Also, the housing 32 can be sized to open/support the vessel as it passes through it. Additionally, the housing 32 can include angled sidewalls sized to just be spaced just off the inner surface of the introducer sheath 10.

The housing 32 and protective coil 35 form a distal retaining member that maintains the position of the occluding device 100 on the flexible guidewire assembly 20 and helps to hold the occluding device 100 in a compressed state prior to its delivery and deployment within a vessel of the vasculature. The protective coil 35 extends from the housing 32 in the direction of the proximal end 23 of the delivery guidewire 21, as shown in FIG. 4. The protective coil 35 is secured to the housing 32 in any known manner. In a first embodiment, the protective coil 35 can be secured to the outer surface of the housing 32. In an alternative embodiment, the protective coil 35 can be secured within an opening of the housing 32 so that the housing 32 surrounds and internally receives the distal end 51 of the protective coil 35 (FIG. 4). As shown in FIGS. 3 and 4, the distal end 102 of the occluding device 100 is retained within the proximal end 52 so that the occluding device 100 cannot deploy while positioned in the sheath 10 or the micro-catheter 1.

At the proximal end of the occluding device 100, a bumper coil 60 and cap 62 prevent lateral movement of the occluding device 100 along the length of the guidewire 21 in the direction of the proximal end 23, see FIG. 3. The bumper coil 60 and cap 62 have an outer diameter $D_4$ of about 0.018 inch to about 0.038 inch. In an embodiment, their outer diameter $D_4$ is about 0.024 inch. The cap 62 contacts the proximal end 107 of the occluding device 100 and prevents it from moving along the length of the guidewire 21 away from the protective coil 35. The bumper coil 60 can be in the form of a spring that contacts and pressures the cap 62 in the direction of the protective coil 35, thereby creating a biasing force against the occluding device 100. This biasing force (pressure) aids in maintaining the secured, covered relationship between the distal end 102 of the occluding device 100 and the protective coil 35. As with any of the coils positioned along the delivery guidewire 21, the bumper coil 60 can be secured, to the delivery guidewire 21 by soldering, welding, RF welding, glue, and/or other known adhesives.

In an alternative embodiment illustrated in FIG. 10, the bumper coil 60 is not utilized. Instead, a proximal end 107 of the occluding device 100 is held in position by a set of spring loaded arms (jaws) 104 while positioned within the introducer sheath 10 or the micro-catheter 1. The inner surfaces of the micro-catheter 1 and the introducer sheath 10 limit the radial expansion of the arms 104. When the proximal end of the occluding device passes out of the micro-catheter 1, the arms 104 would spring open and release the occluding device as shown in FIG. 11.

In an alternative embodiment, the bumper coil 60 and cap 62 can be eliminated and the proximal end of the occluding device 100 can be held in position relative to the protective coil 35 by a tapered section of the guidewire 21. In such an embodiment, the enlarged cross section of this tapered section can be used to retain the occluding device 100 in position along the length of the delivery guidewire 21 and prevent movement of the occluding device 100 in the direction of the proximal end 23.

As shown in FIG. 4, the guidewire assembly 20 includes a support 70 for the occluding device 100. In a first embodiment, the support 70 can include an outer surface of the delivery guidewire 21 that is sized to contact the inner surface of the occluding device 100 when the occluding device 100 is loaded on the guidewire assembly 20. In this embodiment, the outer surface of the delivery guidewire 21 supports the occluding device 100 and maintains it in a ready to deploy state. In another embodiment, illustrated in the Figures, the support 70 comprises a mid-coil 70 that extends from a location proximate the protective coil 35 rearward toward the bumper coil 60. The mid-coil 70 extends under the occluding device 100 and over the delivery guidewire 21, as shown in FIG. 1. The mid-coil 70 can be coextensive with one or more sections of the delivery guidewire 21. For example, the mid-coil 70 could be coextensive with only the second section 24 of the delivery guidewire 21 or it could extend along portions of both the third section 26 and the second section 24 of the delivery guidewire 21.

The mid-coil 70 provides the guidewire assembly 20 with an outwardly extending surface that is sized to contact the inner surface of the occluding device 100 in order to assist in supporting the occluding device and maintaining the occluding device 100 in a ready to deploy state. Like the other coils discussed herein and illustrated in the figures, the coiled form of the mid-coil 70 permits the mid-coil 70 to flex with the delivery guidewire 21 as the delivery guidewire 21 is advanced through the vasculature of the patient. The mid-coil 70 provides a constant diameter along a length of the delivery guidewire 21 that is covered by the occluding device 100 regardless of the taper of the delivery guidewire 21 beneath the occluding device 100. The mid-coil 70 permits the delivery guidewire 21 to be tapered so it can achieve the needed flexibility to follow the path of the vasculature without compromising the support provided to the occluding device 100. The mid-coil 70 provides the occluding device 100 with constant support regardless of the taper of the delivery guidewire 21 prior to the occluding device 100 being deployed. The smallest diameter of the occluding device 100 when in its compressed state is also controlled by the size of the mid-coil 70. Additionally, the diameter of the mid-coil 70 can be chosen so that the proper spacing, including no spacing, is established between the occluding device 100 and the inner wall of the micro-catheter 1 prior to deployment of the occluding device 100. The mid-coil 70 can also be used to bias the occluding device 100 away from the delivery guidewire 21 during its deployment.

In either embodiment, the support 70 can have an outer diameter $D_3$ of about 0.010 inch to about 0.018 inch. In an embodiment, the outer diameter $D_3$ is about 0.014 inch. The support 70 can also have a length $L_3$ of about 2.0 cm to about 30 cm. In an embodiment, the length $L_3$ of the support 70 is about 7 cm.

The occluding device 100 may also be placed on the mid-coil 70 between an optional pair of radio-opaque marker bands located along the length of the guidewire assembly 20. Alternatively, the protective coil 35, bumper coil 60 and or mid-coil 70 can include radio-opaque markers. In an alternative embodiment, the guidewire assembly 20 may include only a single radio-opaque marker. The use of radio-opaque markers allows for the visualization of the guidewire assembly 20 and the occluding device 100 during placement within the vasculature. Such visualization techniques may include conventional methods such as fluoroscopy, radiography, ultra-sonography, magnetic resonance imaging, etc.

The occluding device 100 can be delivered and deployed at the site of an aneurysm A according to the following method and variations thereof. The delivery of the occluding device 100 includes introducing the micro-catheter 1 into the vasculature until it reaches a site that requires treatment. The micro-catheter 1 is introduced into the vasculature using a conventional technique such as being advanced over or simultaneously with a conventional vascular guidewire (not shown). The positioning of the micro-catheter 1 can occur before it receives the guidewire assembly 20 or while it contains the guidewire assembly 20. The position of the micro-catheter 1 within the vasculature can be determined by identifying radio-opaque markers positioned on or in the micro-catheter 1.

After the micro-catheter 1 is positioned at the desired location, the guidewire is removed and the distal end of the introducer sheath 10 is inserted into the proximal end of the micro-catheter 1, as shown in FIG. 1. In an embodiment, the distal end of the introducer sheath 10 is introduced through the hub 2 at the proximal end of the micro-catheter 1. The introducer sheath 10 is advanced within the micro-catheter 1 until a distal tip of the introducer sheath 10 is wedged within the micro-catheter 1. At this position, the introducer sheath 10 cannot be advanced further within the micro-catheter 1. The introducer sheath 10 is then securely held while the delivery guidewire assembly 20 carrying the occluding device 100 is advanced through the introducer sheath 10 until the occluding device 100 is advanced out of the introducer sheath 10 and into the micro-catheter 1.

The guidewire assembly 20 and the occluding device 100 are advanced through the micro-catheter 1 until the tip coil 29 is proximate the distal end of the micro-catheter 1. At this point, the position of the micro-catheter 1 and guidewire assembly 20 can be confirmed. The guidewire assembly 20 is then advanced out of the micro-catheter 1 and into the vasculature of the patient so that the proximal end 107 of the occluding device 100 is positioned outside the distal end of the micro-catheter 1 and adjacent the area to be treated. At any point during these steps, the position of the occluding device 100 can be checked to determine that it will be deployed correctly and at the desired location. This can be accomplished by using the radio-opaque markers discussed above.

Figure 7:
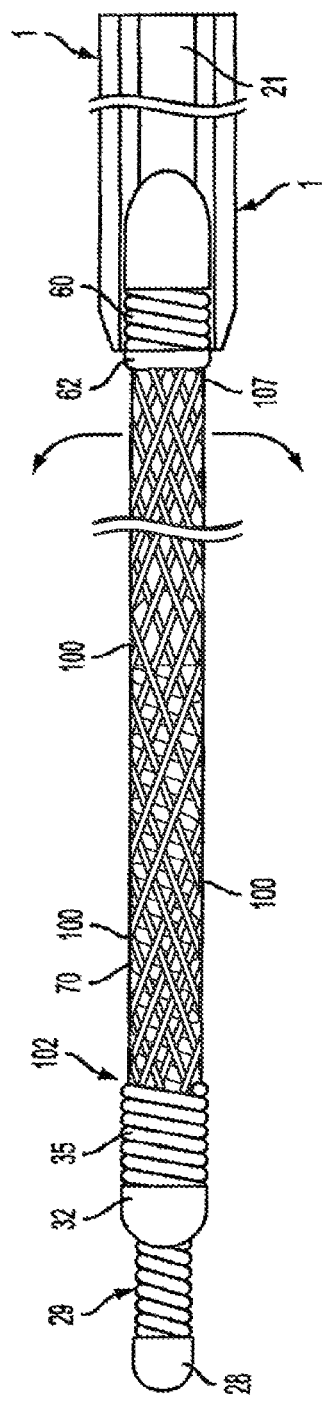
FIG. 7 illustrates the occluding device and a portion of the guidewire assembly positioned outside the catheter, and how a proximal end of the occluding device begins to deploy within a vessel.

When the distal end 102 of the occluding device 100 is positioned outside the micro-catheter 1, the proximal end 107 will begin to expand, in the direction of the arrows shown in FIG. 7, within the vasculature while the distal end 102 remains covered by the protective coil 35. When the occluding device 100 is in the proper position, the delivery guidewire 21 is rotated (See FIG. 8) until the distal end 102 of the occluding device 100 moves away from the protective coil 35 and expands within the vasculature at the desired location. The delivery guidewire 21 can be rotated either clockwise or counter clockwise as needed to deploy the occluding device 100. In an embodiment, the delivery guidewire 21 may be rotated, for example, between two and ten turns in either or both directions. In another example, the occluding device may be deployed by rotating the delivery guidewire 21 clockwise for less than five turns, for example, three to five turns. After the occluding device 100 has been deployed, the delivery guidewire 21 can be retracted into the micro-catheter 100 and removed form the body.

Figure 9:
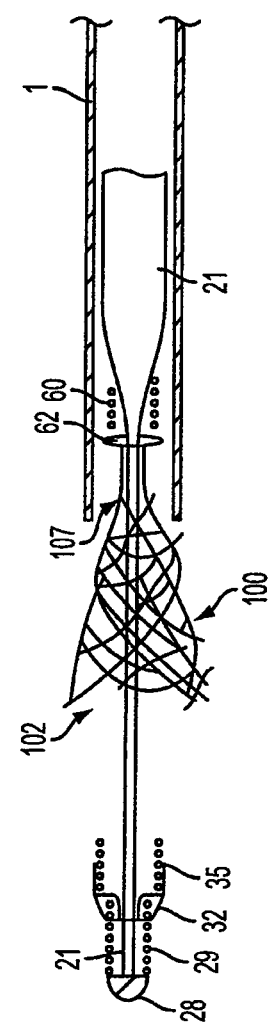
FIG. 9 illustrates the deployment of the occluding device according to an aspect of the present invention.

In an alternative or additional deployment step shown in FIG. 9, friction between the occluding device 100 and inner surface of the micro-catheter 1 cause the distal end of the occluding device 100 to separate from the protective coil 35.

The friction can be created by the opening of the occluding device 100 and/or the mid-coil 70 biasing the occluding device 100 toward the inner surface of the micro-catheter 1. The friction between the micro-catheter 1 and the occluding device 100 will assist in the deployment of the occluding device 100. In those instances when the occluding device 100 does not open and separate from the protective coil 35 during deployment, the friction between occluding device 100 and the inner surface of the micro-catheter 1 will cause the occluding device 100 to move away from the protective coil 35 as the delivery guidewire 21 and the micro-catheter 1 move relative to each other. The delivery guidewire 21 can then be rotated and the occluding device 100 deployed within the vessel.

After the occluding device 100 radially self-expands into gentle, but secure, contact with the walls of the vessel so as to occlude the neck of the aneurysm A, the micro-catheter 1 may be removed entirely from the body of the patient. Alternatively, the micro-catheter 1 may be left in position within vasculature to allow for the insertion of additional tools or the application of drugs near the treatment site.

Known materials can be used in the present invention. One common material that can be used with the occluding device 100 and the guidewire 21 is Nitinol, a nickel-titanium shape memory alloy, which can be formed and annealed, deformed at a low temperature, and recalled to its original shape with heating, such as when deployed at body temperature in the body. The radio-opaque markers can be formed of radio-opaque materials including metals, such as platinum, or doped plastics including bismuth or tungsten to aid in visualization.

The apparatus and methods discussed herein are not limited to the deployment and use within the vascular system but may include any number of further treatment applications. Other treatment sites may include areas or regions of the body such as organ bodies. Modification of each of the above-described apparatus and methods for carrying out the invention, and variations of aspects of the invention that are obvious to those of skill in the art are intended to be within the scope of the claims. Furthermore, no element, component or method step is intended to be dedicated to the public regardless of whether the element, component or method step is explicitly recited in the claims.

What is claimed:

1. A method for delivering a stent to a location within a vessel, said method comprising:
    introducing a delivery assembly into a catheter, the delivery assembly comprising (i) an elongate flexible member; and (ii) a retaining member, at a distal portion of the elongate member, having an inner lumen that extends around a circumference of the elongate member, the lumen receiving a first end of the stent to secure a portion of the stent in the retaining member;
    positioning the stent and a distal end of the catheter proximate an aneurysm within the vessel such that at least a portion of the stent is outside of the distal end of the catheter;
    rotating said retaining member relative to the stent, whereby the first end moves proximally relative to the retaining member and is disengaged from within the lumen while deploying said stent at the aneurysm.

2. The method according to claim 1, further comprising the step of removing the delivery assembly from within the catheter.

3. The method according to claim 1, further comprising the step of removing the catheter from within the vessel.

4. The method according to claim 1, further comprising the step of confirming the position of said stent prior to deploying said stent.

5. The method according to claim 1, wherein the stent is self-expanding.

6. The method according to claim 1, wherein the retaining member comprises a protective coil.

7. The method according to claim 1, further comprising limiting proximal movement of a second end of the stent along a length of the elongate member.

8. The method according to claim 1, wherein the first end of the stent is biased radially outwardly against the retaining member.

9. The method according to claim 1, wherein the delivery assembly further comprises a proximal member configured to limit proximal movement of a second end of the stent along a length of the flexible member, the method further comprising maintaining the retaining member and the proximal member substantially fixed axially with respect to each other while the stent is released from the lumen.

10. A method for positioning a self-expanding device at a treatment site in a vessel, the method comprising:
    introducing a catheter and a delivery assembly into the vessel, the delivery assembly comprising an elongate flexible member including a retaining member receiving a first end of the self-expanding device, the self-expanding device being concentrically within the retaining member and biased against a surface positioned about a lumen of the retaining member; and
    positioning the catheter and the delivery assembly such that the retaining member and at least a portion of the self-expanding device are outside a distal end of the catheter and such that a second end of the self-expanding device is expanded toward a wall of the vessel;
    rotating the retaining member so as to release the first end of the self-expanding device from the retaining member by moving the first end proximally relative to the retaining member.

11. The method according to claim 10, wherein the treatment site comprises an aneurysm.

12. The method according to claim 10, wherein the retaining member comprises a protective coil, and the self-expanding device is received within an interior of the protective coil.

13. The method according to claim 10, further comprising removing the delivery assembly proximally through the catheter and leaving the self-expanding device in the vessel.

14. A method for delivering a self-expanding device in a body lumen, the method comprising:
    providing a delivery assembly positioned at least partially within an introducer sheath, the delivery assembly comprising an elongate flexible member and a retaining member at a distal portion of the delivery assembly, the elongate flexible member extending through the retaining member, the retaining member having a lumen therein extending around the elongate flexible member, the retaining member receiving a first end of the self-expanding device within the lumen, the self-expanding device being biased radially outward against the retaining member;
    advancing at least a portion of the delivery assembly through the introducer sheath and into a catheter;
    positioning the delivery assembly and the catheter at least partially within the body lumen such that the retaining member is outside a distal end of the catheter and at least a portion of the self-expanding device extends distal of the distal end of the catheter and such that a second end of the self-expanding device is expanded toward a wall of the body lumen;

rotating the retaining member, whereby the first end moves proximally relative to the retaining member so as to release the first end from within the retaining member.

15. The method according to claim 14, wherein the assembly further comprises a second retaining member receiving a second end of the self-expanding device, the method further comprising releasing the second end of the self-expanding device from the second retaining member.

16. The method according to claim 14, wherein the retaining member comprises a protective coil, the self-expanding device received within an interior of the protective coil.

17. The method according to claim 14, further comprising inserting a distal end of the introducer sheath into a proximal end of the catheter, and removing the introducer sheath from the catheter after advancing the delivery assembly through the introducer sheath into the catheter.

18. The method according to claim 14, further comprising removing the delivery assembly proximally through the catheter and leaving the self-expanding device in the body lumen.

\* \* \* \* \*